United States Patent
Folk

(10) Patent No.: US 9,456,834 B2
(45) Date of Patent: Oct. 4, 2016

(54) THROMBECTOMY DEVICE WITH DISTAL PROTECTION

(71) Applicant: COVIDIEN LP, Mansfield, MA (US)

(72) Inventor: Chris Folk, Los Angeles, CA (US)

(73) Assignee: Covidien LP, Mansfield, MA (US)

( * ) Notice: Subject to any disclaimer, the term of this patent is extended or adjusted under 35 U.S.C. 154(b) by 663 days.

(21) Appl. No.: 13/664,802

(22) Filed: Oct. 31, 2012

(65) Prior Publication Data

US 2014/0121672 A1 May 1, 2014

(51) Int. Cl.
| | |
|---|---|
| *A61B 17/221* | (2006.01) |
| *A61F 2/01* | (2006.01) |
| *A61F 2/915* | (2013.01) |
| *A61B 17/22* | (2006.01) |

(52) U.S. Cl.
CPC ............ *A61B 17/221* (2013.01); *A61F 2/013* (2013.01); *A61B 2017/2212* (2013.01); *A61B 2017/22034* (2013.01); *A61F 2002/016* (2013.01); *A61F 2002/018* (2013.01); *A61F 2002/91558* (2013.01)

(58) Field of Classification Search
CPC .................. A61B 17/221; A61B 2017/2212; A61B 2002/016; A61B 2002/018
See application file for complete search history.

(56) References Cited

U.S. PATENT DOCUMENTS

| | | |
|---|---|---|
| 5,749,880 A | 5/1998 | Banas et al. |
| 5,800,519 A | 9/1998 | Sandock |
| 5,827,324 A | 10/1998 | Cassell et al. |
| 5,941,896 A | 8/1999 | Kerr |
| 5,947,995 A | 9/1999 | Samuels |
| 6,231,598 B1 | 5/2001 | Berry et al. |
| 6,254,628 B1 | 7/2001 | Wallace et al. |
| 6,258,115 B1 | 7/2001 | Dubrul |
| 6,402,771 B1 | 6/2002 | Palmer et al. |
| 6,458,139 B1 | 10/2002 | Palmer et al. |
| 6,558,405 B1 | 5/2003 | McInnes |
| 6,991,641 B2 | 1/2006 | Diaz et al. |
| 7,041,116 B2 | 5/2006 | Goto et al. |
| 7,261,727 B2 | 8/2007 | Thielen |

(Continued)

FOREIGN PATENT DOCUMENTS

| | | |
|---|---|---|
| CN | 1308508 A | 8/2001 |
| CN | 1663536 A | 9/2005 |

(Continued)

OTHER PUBLICATIONS

U.S. Appl. No. 13/950,930, filed Jul. 25, 2013.

*Primary Examiner* — Thomas McEvoy

(74) *Attorney, Agent, or Firm* — Mark J. Kertz, Esq.

(57) ABSTRACT

A vascular device is provided that includes a frame attached to a distal end of a delivery wire. The frame includes a cylindrical body formed of a plurality of interconnecting members, the interconnecting members being configured to exert a first radial force against an inner wall of an anatomical lumen. The vascular device further includes a protector having a proximal end, a distal end, and a profile that tapers distally from a proximal cross-sectional dimension to a reduced distal cross-sectional dimension. The protector is coupled to a distal end of the frame via a plurality of connecting members, each of the members extending from a distal end of a corresponding interconnecting member and converging distally to form a taper. The connecting members are configured to exert a second radial force, less than the first radial force, against the inner wall of the lumen.

24 Claims, 8 Drawing Sheets

(56) References Cited

U.S. PATENT DOCUMENTS

| | | |
|---|---|---|
| 7,344,549 B2 | 3/2008 | Boyle et al. |
| 7,344,550 B2 | 3/2008 | Carrison et al. |
| 7,749,243 B2 | 7/2010 | Phung et al. |
| 8,029,530 B2 | 10/2011 | Gesswein et al. |
| 2001/0025195 A1 | 9/2001 | Shaolian et al. |
| 2002/0004667 A1 | 1/2002 | Adams et al. |
| 2003/0004536 A1 | 1/2003 | Boylan et al. |
| 2003/0004541 A1 | 1/2003 | Linder et al. |
| 2003/0074050 A1 | 4/2003 | Kerr |
| 2003/0195554 A1 | 10/2003 | Shen et al. |
| 2004/0006370 A1 | 1/2004 | Tsugita |
| 2004/0039412 A1 | 2/2004 | Isshiki et al. |
| 2004/0088000 A1 | 5/2004 | Muller |
| 2004/0153117 A1 | 8/2004 | Clubb et al. |
| 2004/0167568 A1* | 8/2004 | Boyle ............... A61F 2/013 606/200 |
| 2004/0193208 A1 | 9/2004 | Talpade et al. |
| 2005/0038447 A1 | 2/2005 | Huffmaster |
| 2005/0055047 A1 | 3/2005 | Greenhalgh |
| 2005/0131449 A1 | 6/2005 | Salahieh et al. |
| 2005/0209678 A1 | 9/2005 | Henkes et al. |
| 2005/0283166 A1 | 12/2005 | Greenhalgh |
| 2006/0122643 A1 | 6/2006 | Wasicek |
| 2006/0282116 A1 | 12/2006 | Lowe et al. |
| 2007/0060945 A1 | 3/2007 | Gilson et al. |
| 2007/0208367 A1 | 9/2007 | Fiorella et al. |
| 2007/0219579 A1 | 9/2007 | Paul |
| 2007/0288054 A1 | 12/2007 | Tanaka et al. |
| 2008/0091231 A1 | 4/2008 | Boyle et al. |
| 2008/0208245 A1 | 8/2008 | Hoffman |
| 2009/0105722 A1 | 4/2009 | Fulkerson et al. |
| 2009/0240213 A1 | 9/2009 | Miyagawa et al. |
| 2009/0240238 A1 | 9/2009 | Grodrian et al. |
| 2010/0016946 A1 | 1/2010 | McDermott |
| 2010/0087908 A1 | 4/2010 | Hilaire et al. |
| 2010/0106178 A1* | 4/2010 | Obermiller et al. ......... 606/194 |
| 2010/0168786 A1 | 7/2010 | Dower |
| 2010/0268264 A1 | 10/2010 | Bonnette et al. |
| 2011/0060212 A1 | 3/2011 | Slee et al. |
| 2011/0257675 A1 | 10/2011 | Mackiewicz |
| 2011/0295304 A1 | 12/2011 | Jonsson |
| 2012/0022634 A1 | 1/2012 | Kusleika et al. |
| 2012/0035650 A1 | 2/2012 | Linder et al. |
| 2012/0083868 A1 | 4/2012 | Shrivastava et al. |
| 2012/0245671 A1 | 9/2012 | Wainwright et al. |
| 2012/0265238 A1 | 10/2012 | Hopkins et al. |
| 2012/0330346 A1 | 12/2012 | Frimerman |
| 2013/0345739 A1* | 12/2013 | Brady et al. ............... 606/200 |
| 2014/0088634 A1 | 3/2014 | Sanati |

FOREIGN PATENT DOCUMENTS

| | | |
|---|---|---|
| CN | 101147705 A | 3/2008 |
| CN | 101616639 A | 12/2009 |
| WO | WO-99/44542 A2 | 9/1999 |
| WO | WO-2012/120490 A2 | 9/2012 |

* cited by examiner

THROMBECTOMY DEVICE WITH DISTAL PROTECTION

BACKGROUND

Occlusion of a blood vessel can be caused by a thrombus (i.e., blood clot) that forms in the blood vessel, or by an embolus, i.e., a blood clot that travels downstream. The blockage disrupts blood flow, which prevents oxygen and nutrients from being delivered to their intended locations. Tissue distal to a blood clot that is deprived of oxygen and nutrients can no longer function properly. For every minute that treatment is delayed, additional cellular death of critical tissue can occur.

Current technology for blood flow restoration, for example for treating cerebral arteries occluded by thrombi, can often take hours to reestablish flow in the artery, and can lead to unintended complications. Apparatus and methods for treating cerebral thrombi are often ineffective or only partially effective at resolving thrombus removal, and may result in distal embolization or embolization of uninvolved arteries. For example, some current devices are designed to pierce through a thrombus, or are designed to deploy distally to the thrombus before engaging the thrombus. These devices often fail to capture all of a thrombus, can damage vessel walls distal of a thrombus, can be difficult to maneuver, can unintentionally dislodge portions of a thrombus prior to capture, and/or can take significant amounts of time to restore blood flow. Dislodgment of portions of the thrombus, referred to as secondary emboli, often cause complications because the secondary emboli may travel downstream and occlude other vessels or arteries.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1 and 17. The other clauses can be presented in a similar manner.

1. A vascular device, comprising:
   a frame attached to a distal end of a delivery wire, the frame comprising a cylindrical body formed of a plurality of interconnecting members, the interconnecting members being configured to exert a first radial force against an inner wall of an anatomical lumen; and
   a protector having a proximal end, a distal end, and a profile that tapers distally from a proximal cross-sectional dimension to a reduced distal cross-sectional dimension, the protector being coupled to a distal end of the frame via a plurality of connecting members, each of the members extending from a distal end of a corresponding interconnecting member and converging distally to form a taper, the connecting members being configured to exert a second radial force, less than the first radial force, against the inner wall of the lumen.

2. The vascular device of clause 1, wherein a proximal portion of the plurality of connecting members form a greater cross-sectional dimension than does the cylindrical body.

3. The vascular device of clause 1, wherein a proximal end of the connecting members tapers proximally radially inward without converging to a central longitudinal axis of the frame.

4. The vascular device of clause 1, wherein each of the connecting members comprise a curve having a positive slope, negative slope, and an apex.

5. The vascular device of clause 4, wherein the positive and negative slopes are configured to facilitate deflection of the protector as the protector is advanced in the anatomical lumen.

6. The vascular device of clause 4, wherein the interconnecting members of the frame radially expand to a first diameter, and the connecting members radially expand to a second diameter, greater than the first diameter, wherein the second diameter is formed of apexes of each of the connecting members.

7. The vascular device of clause 1, wherein each of the connecting members comprise a pivot, the pivot having a reduced cross section that permits the protector to radially expand independent of a radial expansion of the frame.

8. The vascular device of clause 1, wherein the protector is coupled to the frame by a chain comprising a plurality of links that permit the protector to radially expand independently of a radial expansion of the frame.

9. The vascular device of clause 8, wherein the links are non-ridgidly joined to each other so that the chain is highly laterally flexible but strong in longitudinal tension.

10. The vascular device of clause 8, wherein the chain is micromachined.

11. The vascular device of clause 1, wherein the protector further comprises a mesh.

12. The vascular device of clause 11, wherein the mesh comprises a plurality of pores sized such that the mesh is configured to capture emboli without preventing blood flow past the mesh.

13. The vascular device of clause 12, wherein the plurality of pores each have a pore size of about 70-200 µm.

14. The vascular device of clause 11, wherein the protector further comprises a collapsible hoop coupled to the mesh and the plurality of connecting members and disposed substantially perpendicular to a central longitudinal axis of the frame.

15. The vascular device of clause 14, wherein the hoop is coupled to the connecting members at a radial apex of the connecting members.

16. The vascular device of clause 11; wherein each of the connecting members comprise a curvature providing a sloped surface proximal of the mesh, the sloped surface being configured to assist the protector in conforming to the inner wall of the anatomical lumen as the vascular device is advanced in the lumen.

17. A method for restricting downstream travel of secondary emboli during thrombus retrieval, the method comprising:
   advancing a microcatheter through a distal end of a guide catheter positioned in an anatomical lumen;
   advancing a vascular device through the microcatheter such that a distal portion of the device is located adjacent a treatment site in the lumen, the device comprising:
   a frame attached to a distal end of a delivery wire, the frame comprising a cylindrical body formed of a plurality of interconnecting members, the interconnecting members being configured to exert a first radial force against an inner wall of the lumen; and a protector coupled to a distal end of the frame via a plurality of connecting members, each of the members extending from a distal end of a corresponding interconnecting member and converging distally to form a taper, the connecting members being configured to exert a second radial force, less than the first radial force, against the inner wall of the lumen;

withdrawing the microcatheter relative to the device to expose the device, thereby permitting the frame to expand against a length of the thrombus and engage the thrombus;

retrieving the thrombus by moving the device relative to the guide catheter until the guide catheter covers a portion of the frame; and restricting downstream travel of secondary emboli during the expanding of the frame and the retrieval of the thrombus by capturing the secondary emboli in the protector.

18. The method of clause 17, wherein the connecting members comprise a sloped surface that permits the protector to conform to the inner wall of the lumen as the device is moved in the lumen.

19. The method of clause 18, wherein the sloped surface comprises a curve having a positive slope, negative slope, and an apex.

20. The method of clause 17, further comprising minimizing gaps from forming between the inner wall of the lumen and the protector by radially expanding the protector to a diameter larger than a greatest diameter of the frame.

21. The method of clause 17, wherein the protector radially expands independent of the frame.

22. The method of clause 17, wherein the protector is coupled to the frame by a chain.

23. The method of clause 22, wherein the chain comprises a plurality of links that are non-ridgidly joined to each other.

24. The method of clause 17, wherein the restricting downstream travel comprises capturing the secondary emboli with a mesh attached to the protector, the mesh comprising a plurality of pores sized to capture the secondary emboli without preventing blood flow in the lumen past the protector.

25. The method of clause 17, further comprising collapsing the protector by moving the device relative to the guide catheter until the guide catheter covers a portion of the protector, wherein the guide catheter deflects the connecting members, thereby causing the protector to collapse.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

Current technology for blood flow restoration, for example for treating cerebral arteries occluded by thrombi, can often take hours to reestablish flow in the artery, and can lead to unintended complications. Apparatus and methods for treating cerebral thrombi are often ineffective or only partially effective at resolving thrombus removal, and may result in distal embolization or embolization of uninvolved arteries. For example, some current devices are designed to pierce through a thrombus, or are designed to deploy distally to the thrombus before engaging the thrombus. These devices often fail to capture all of a thrombus, can damage vessel walls distal of a thrombus, can be difficult to maneuver, can unintentionally dislodge portions of a thrombus prior to capture, and/or can take significant amounts of time to restore blood flow. Dislodgment of portions of the thrombus, referred to as secondary emboli, often cause complications because the secondary emboli may travel downstream and occlude other vessels or arteries.

The medical devices of the subject technology solves some or all of the foregoing problems by preventing secondary emboli from traveling downstream during thrombus retrieval. The medical devices include a distal portion that is designed to capture the secondary emboli, and therefore, prevent the secondary emboli from traveling downstream during clot retrieval.

The medical device comprises a frame configured to apply a radial force against an inner wall of a lumen by utilizing various suitable means. For example, the medical device may be a self-expanding stent and/or a balloon-expandable stent. In some embodiments, "vessel" or "lumen" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. As will be seen below, the medical device includes a distal portion configured to capture secondary emboli during thrombus retrieval.

Figure 1:
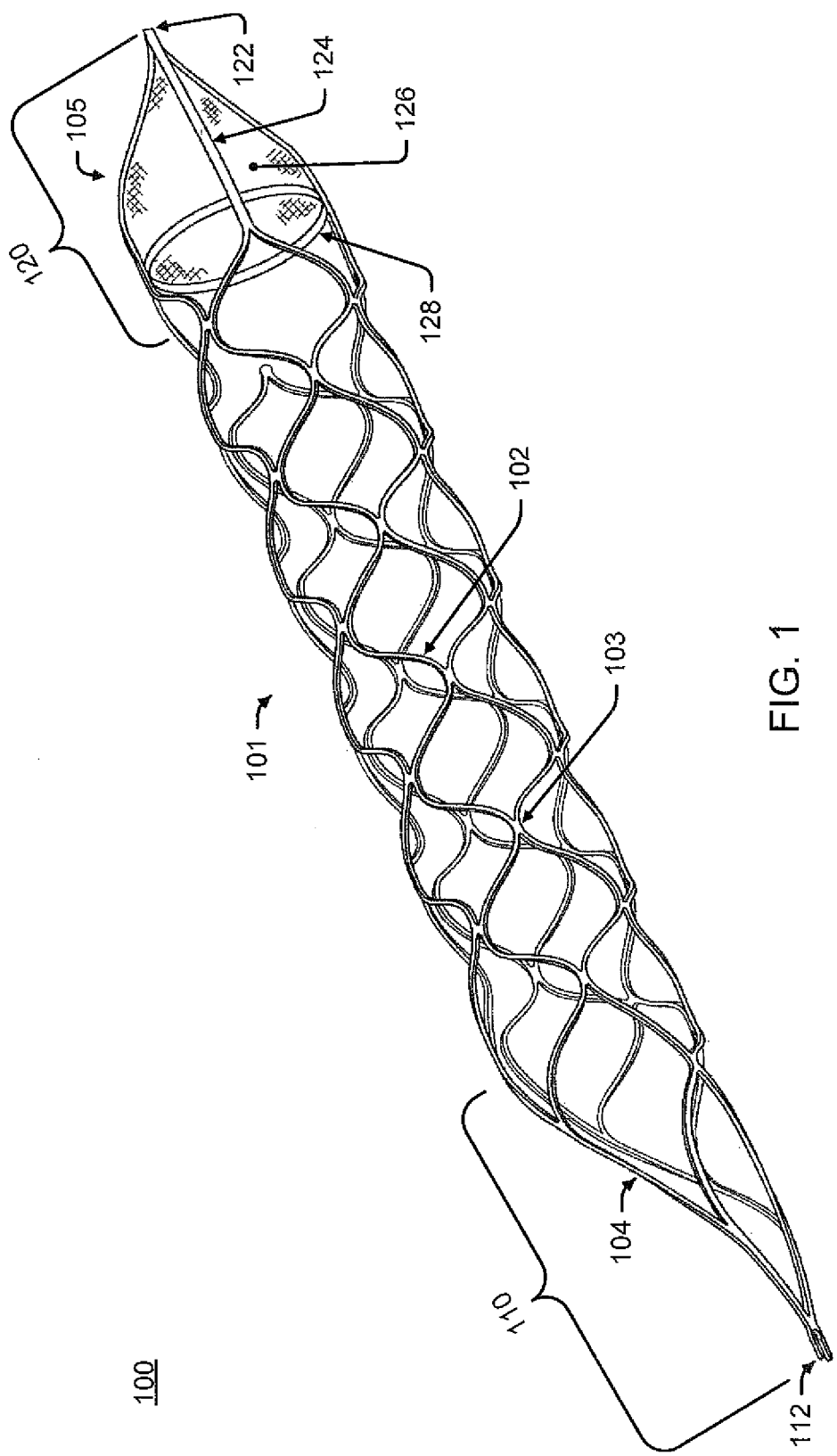
FIG. 1 depicts a medical device according to some embodiments of the subject technology.

FIG. 1 depicts a medical device 100 according to some embodiments of the subject technology. The medical device 100 includes a frame 101 having a proximal portion 110 and a distal portion 120. The frame comprises a cylindrical body formed of a plurality of interconnecting members 102. The interconnecting members 102 may comprise undulating members which extend in a generally longitudinal direction. The interconnecting members 102 may be connected to each other by a plurality of joints 103, to thereby form a substantially cylindrical shape. The joints 103 may be formed by welding, soldering, or otherwise joining the interconnecting members 102. Alternatively, the medical device 100 may be formed, for example, by laser cutting a pre-formed tube or sheet, by interconnecting a multitude of members by laser welding, or by other suitable methods such as electrochemical etching, grinding, piercing, electroforming, or other means.

The proximal portion 110 includes a tapered section 104 extending from the frame 101 toward a proximal end 112. The proximal end 112 includes a connection mechanism configured to attach the frame 101 to a distal end of a delivery wire. The proximal end 112 may be constructed from a radiopaque material or include a radiopaque marker allowing in vivo imaging of the medical device 100.

The connection mechanism may include a generally non-detachable interface or transition point between the medical device 100 and the delivery wire. In some embodiments the connection mechanism may be integrally formed with the delivery wire and/or the medical device 100. Depending on the procedure and intended use of the medical device 100, it may be advantageous to have a connection mechanism that permits release of the medical device 100. For example, during a blood flow restoration procedure, it may prove difficult and/or dangerous to fully retrieve a thrombus due to a complicated vasculature or the risk of damaging a lumen wall. Leaving the medical device 100 behind may prove to be the only option available to a surgeon or other medical personnel. In other circumstances the medical device 100 may include drug-eluding capabilities, and/or may be coated with a particular type of drug that facilitates thrombus dissolution. It may be advantageous in such circumstances to release the medical device 100 and allow the medical device 100 to anchor the thrombus against the lumen wall while the thrombus is dissolved by the drug.

The distal portion 120 includes a protector 105 having a proximal end 121 and a distal end 122. The protector 105 is coupled to a distal end of the frame 101 via a plurality of connecting members 124. For example, each of the connecting members 124 may extend from a distal end 106 of a corresponding interconnecting member 102, and converge distally to form a taper.

The protector includes a mesh 126. The mesh 126 is disposed between the connecting members 124, thereby forming an area to capture emboli during clot retrieval. The mesh 126 may be coupled to the connecting members 124 with adhesive, solder, weld, or other suitable means of attachment. The mesh may comprise a plurality of pores sized such that the mesh 126 is configured to capture emboli without preventing blood from flowing through the mesh 126. For example, the plurality of pores of the mesh 126 may each have a pore size of about 70-200 μm.

In one aspect, the protector 105 may include a collapsible hoop 128. The hoop 128 is disposed at the proximal end 121 of the protector 105 and disposed substantially perpendicular to a central longitudinal axis of the frame 101. The hoop 128 is coupled to the mesh 126 and the connecting members 124. The hoop 128 may be coupled to the mesh 128 and the connecting members 124 with adhesive, solder, weld, or other suitable means of attachment. In one aspect, the hoop 128 assists in deploying the protector 105 and/or the mesh 128, such that upon deployment, the mesh 128 is in an expanded configuration and capable of capturing emboli within the area formed by the mesh 128. In one aspect, the hoop 128 may be coupled to the connecting members 124 at a radial apex of the connecting members 124, as described further below.

Figure 2A:
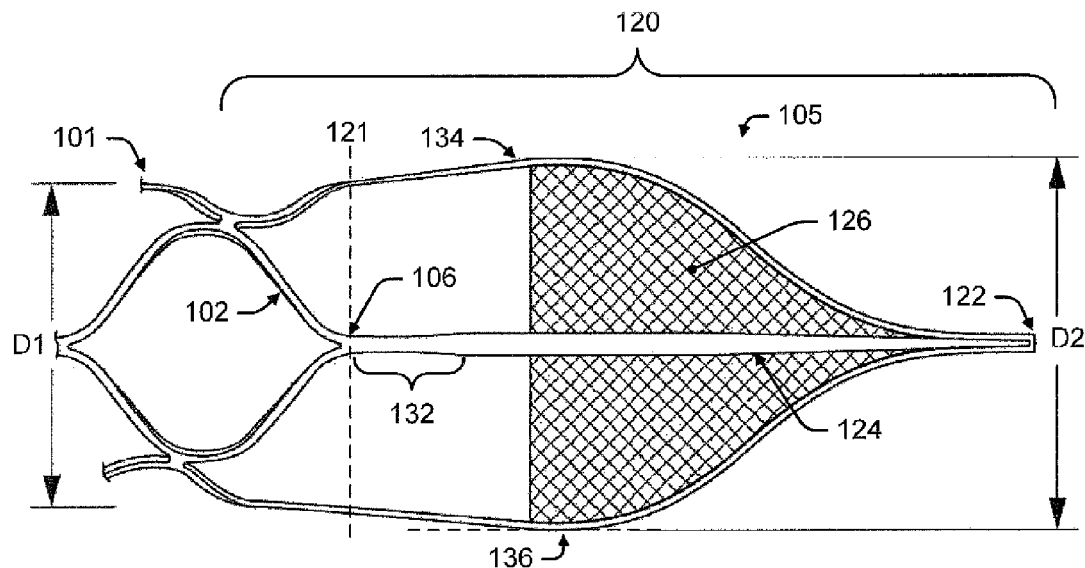
FIG. 2A depicts a side view of a distal portion of a medical device according to some embodiments of the subject technology.

FIG. 2A depicts a side view of the distal portion 120 of the medical device 100, according to some embodiments of the subject technology. The protector 105 may have a general profile that includes a taper that extends distally from a proximal cross-sectional dimension to a reduced distal cross-sectional dimension. The taper may be formed by the connecting members 124.

In one aspect, the taper formed by the connecting members 124 may comprise a curve 134 having a positive slope, negative slope, and an apex 136. The positive and negative slopes of the connecting members 124 may be configured to facilitate deflection of the protector 105 as the protector 105 is advanced in the anatomical lumen. For example, from the proximal end 121 of the protector 105, each of the connecting members 124 may extend distally, radially outward, toward the apexes 136. The portion of the connecting members 124 between the proximal end 121 and the apexes 136 have a positive slope. From the apexes 136, each of the connecting members 124 converge distally, radially inward, toward the distal end 122. The portion of the connecting members 124 between the apexes 136 and the distal end 122 have a negative slope. The connecting members 124 converging to the distal end 122 may be joined to one another at the distal end 122. In another example, the connecting members 124 converging to the distal end 122 may be arranged in an overlapping configuration and be unattached to each other at the distal end 122. By being unattached to adjacent connecting members 124 at the distal end 122, the connecting members 124 may facilitate deployment and/or resheathing of the medical device 100 from a microcatheter by allowing the connecting members 124 to slide relative to each other at the distal end 122.

In other words, the protector 105 may have a profile that includes a first taper that extends proximally radially inward from the apex 136 to the proximal end 121, a cross sectional diameter of the protector 105 at the apex 136 being larger than a cross sectional diameter of the protector 105 at the proximal end 121. In one aspect, because the connecting members 124 taper proximally radially inward from the apexes 136 to the distal end 106 of the corresponding interconnecting member 102, the connecting members 124 do not converge to a central longitudinal axis of the frame 101. The profile also includes a second taper that extends distally radially inward from the apexes 136 to the distal end 122, a cross sectional diameter of the protector 105 at the distal end 122 being smaller than the cross sectional diameter of the protector 105 at the apex 136 and the proximal end 121.

In one aspect, because of the sloped surface created by the curvature 134 of the connecting members 124 proximal of the mesh 126, the protector 105 may be deflected to conform to the inner wall of the anatomical lumen as the medical device 100 is advanced in the lumen. Thus, as the anatomical lumen changes in diameter, the protector 105 is deflected by the sloped surface of the connecting members 124 to reduce the diameter of the protector 105, as discussed further below.

In one aspect, the protector 105 has a larger diameter than the frame 101 in order to prevent emboli from passing between an inner wall of the anatomical lumen and an outer surface of the protector 105. For example, a proximal portion of the plurality of connecting members 124 may form a greater cross-sectional dimension than does the cylindrical body formed by the frame 101. Specifically, because each of the connecting member 124 extends distally and radially outward from the distal ends 106 of the interconnecting members 102, to the apex 136, the protector 105 has a larger cross-sectional dimension than the cylindrical body formed by the frame 101.

The protector 105 has its largest diameter at the apexes 136. For example, the interconnecting members 102 of the frame 101 radially expand to a first diameter D1, and the connecting members 124 radially expand to a second diameter D2, formed of the apexes 136 of each of the connecting members 124. The second diameter D2 is greater than the first diameter D1, and is greater than all other diameters of the medical device 100.

In another aspect, even though the connecting members 124 have a curvature 134 that forms a larger cross sectional diameter at the apexes 136, the connecting members 124 exert a radial force against the inner wall of the anatomical lumen that is less than a radial force exerted by the interconnecting members 102 against the inner wall of the anatomical lumen. The frame 101 may be designed to generate specific forces once it is deployed and released from a microcatheter in order to optimally engage and remove a wide range of both soft and hard thrombi. By deploying the frame 101 across a thrombus, the frame 101 may self-expand to a diameter due to elastic energy stored in the interconnecting members 102. The frame 101 may expand in the anatomical lumen until equilibrium is reached between the stored elastic energy and an opposing force from the surrounding inner wall of the anatomical lumen and/or the thrombus. The interconnecting members 102 of the medical device 100 may penetrate the thrombus, promoting adhesion and embedment of the thrombus to the frame 101, and the expanding force of the interconnecting members 102 may promote dislodgment of the thrombus from the inner wall of the anatomical lumen.

The protector 105 may be designed to generate a force once it is deployed and released from a microcatheter, that is less than the force generated by the frame 101. The reduced force of the protector 105 allows the protector 105 to deflect and conform to the inner wall of the anatomical lumen with less opposing force from the inner wall of the anatomical lumen. By deploying the protector 105 distal of the thrombus, the protector may self-expand to a larger diameter than the frame, due to elastic energy stored in the connecting members 124. The protector 105 may expand in the anatomical lumen until equilibrium is reached between the stored elastic energy and an opposing force from the surrounding inner wall of the anatomical lumen.

For example, the stored elastic energy of the frame 101 and the protector 105 may generate an outward force known as a radial force. The radial force is equivalent to the outward force exerted by the frame 101 or the protector 105 during compression. In some aspects, the radial force of the frame 101 may be designed so that it is high enough to resist compression forces from the surrounding inner wall of the anatomical lumen, maintain patency of the frame 101, and restore flow through the thrombus site. The radial force of the protector 105 may be designed so that it is less than the radial force of the frame, such that compression forces from the surrounding inner wall of the anatomical lumen cause the protector to deform and conform to the inner wall of the anatomical lumen.

The frame 101 may have a radial force measurement greater than or equal to 0.0010 N per mm of length of the portion of the frame 101 that is configured to contact the inner wall of the anatomical lumen or the thrombus. The protector 105 may have a radial force measurement in a range of about 0.0006-0.0009 N per mm of length of the portion of the protector 105 that is configured to contact the inner wall of the anatomical lumen. In another example, the radial force measurement may be less than 0.0006 N per mm or be in a range of about 0.0009-0.0010 N per mm. The length in this unit refers to a proximal to distal direction measurement.

In another aspect, the protector 105 may radially expand independent of a radial expansion of the frame 101. For example, the connecting members 124 may comprise a pivot 132 having a reduced cross section that permits the protector 105 to radially expand independent of the radial expansion of the frame 101. The reduced cross section of the pivot 132 is prone to bend and deflect, thereby allowing the protector 105 to radially expand independent of the frame 101.

Figure 2B:
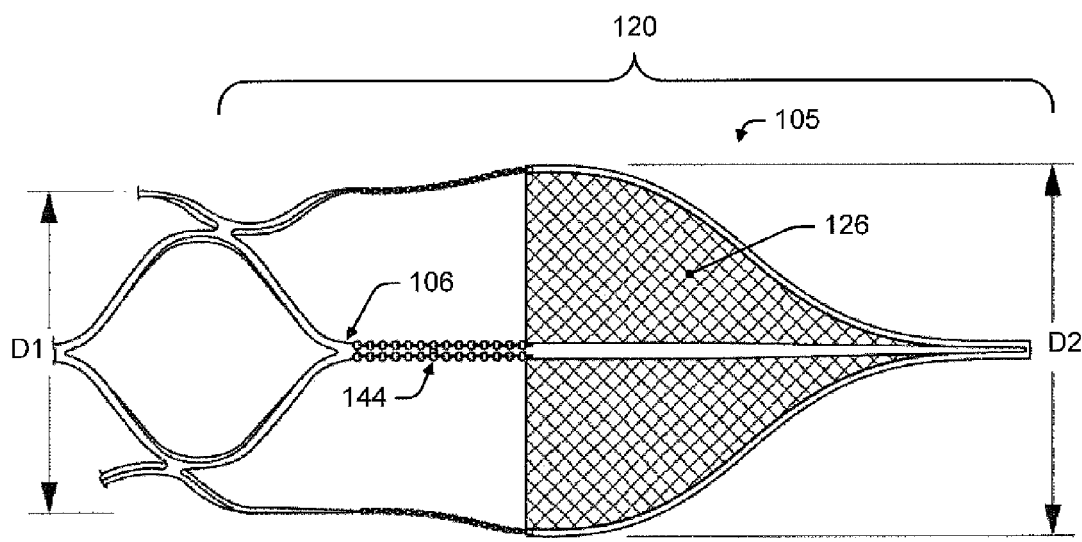
FIG. 2B depicts a side view of a distal portion of a medical device according to some embodiments of the subject technology.

Referring to FIG. 2B, the protector 105 may be coupled to the frame 101 by a chain 144 comprising a plurality of links that permit the protector 105 to radially expand independently of the radial expansion of the frame 101. The links of the chain 144 are non-ridgidly joined to each other so that the chain is highly laterally flexible but strong in longitudinal tension. In one aspect, the chain 144 is micromachined. The chain 144 may extend from the distal end 106 of the interconnecting members 102 to the proximal end of the mesh 126. Each chain 144 may comprise two individual rows, each row coupled to the other via a chain link disposed substantially at a center portion of the row. The chain 144 may be coupled to the distal end 106 of the interconnecting members 102 and the proximal end of the mesh 126 by adhesive, weld, solder, fasteners, or other suitable means for attachment.

Radiopaque markers may be located adjacent the proximal or distal ends 112, 122 or both, and may be located at any position along the length of the medical device 100 between the proximal and distal ends 112, 122. The markers may be attached to the medical device 100 by techniques such as adhesives, heat fusion, interference fit, fasteners, intermediate members, coatings, or by other techniques.

In some embodiments, the markers are comprised of ultrasonic markers, MRI safe markers, or other markers. In some embodiments ultrasonic markers permit a physician to accurately determine the position of the medical device 100 within a patient under ultrasonic visualization. Materials for an ultrasonic marker have an acoustical density sufficiently different from the medical device 100 to provide suitable visualization via ultrasonic techniques. Exemplary materials comprise polymers, metals such as tantalum, platinum, gold, tungsten and alloys of such metals, hollow glass spheres or microspheres, and other materials.

In some embodiments, MRI safe markers permit a physician to accurately determine the position of the medical device 100 within a patient under magnetic resonance imaging. Exemplary materials for making MRI safe marker have a magnetic signature sufficiently different from the medical device 100 to provide suitable visualization via MRI techniques. Exemplary materials comprise polymers, metals such as tantalum, platinum, gold, tungsten and alloys of such metals, non-ferrous materials, and other materials.

Figure 3:
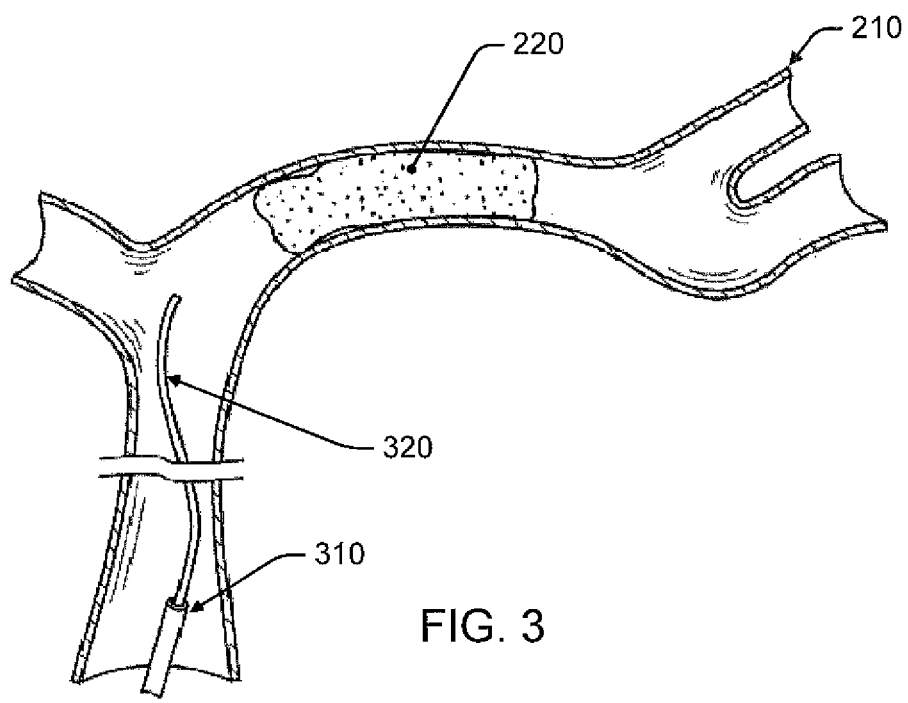
FIG. 3 depicts a cross section view of a vessel and delivery of a medical device according to some embodiments of the subject technology.
Figure 4:
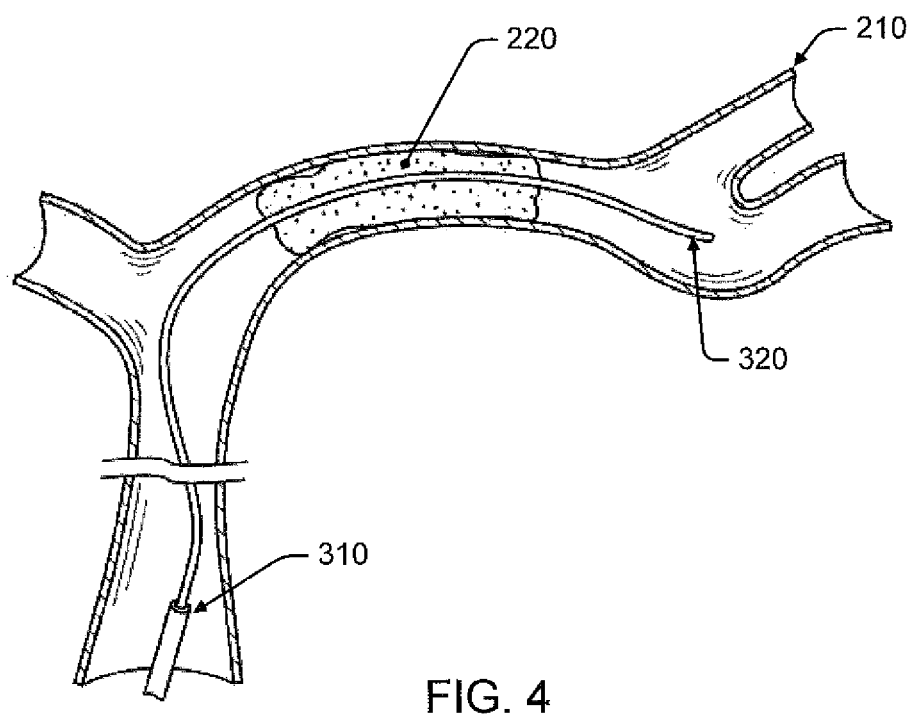
FIG. 4 depicts a cross section view of a vessel and delivery of a medical device according to some embodiments of the subject technology.
Figure 5:
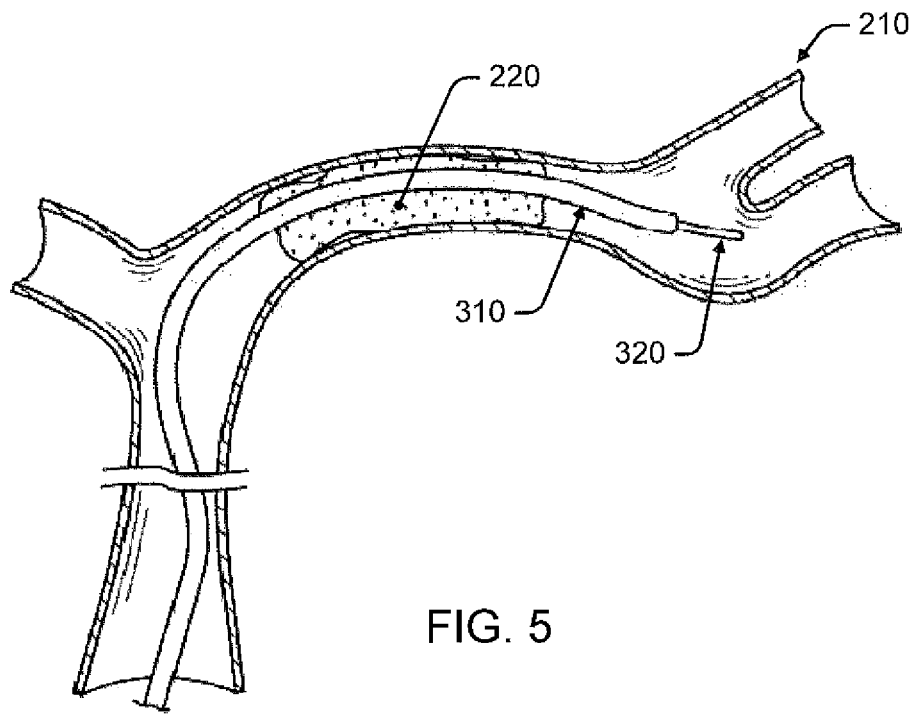
FIG. 5 depicts a cross section view of a vessel and delivery of a medical device according to some embodiments of the subject technology.

A technique for engaging and removing a thrombus 220 and restricting downstream travel of secondary emboli during thrombus retrieval will now be discussed with reference to FIGS. 3-13. Referring to FIG. 3, the medical device 100 may be inserted into an anatomical lumen 210 by first inserting a guide wire 320 into the anatomical lumen 210. The guide wire 320 is advanced through a guide catheter and a microcatheter 310 to the treatment site, adjacent the thrombus 220. Referring to FIG. 4, the guide wire 320 is advanced distally through the thrombus 220. Once in position, the microcatheter 310 is advanced over the guide wire 320, through a distal end of the guide catheter, into the anatomical lumen 210. Referring to FIG. 5, the microcatheter 310 is advanced distally through the thrombus 220. The guide wire 320 is then withdrawn proximally.

Figure 6:
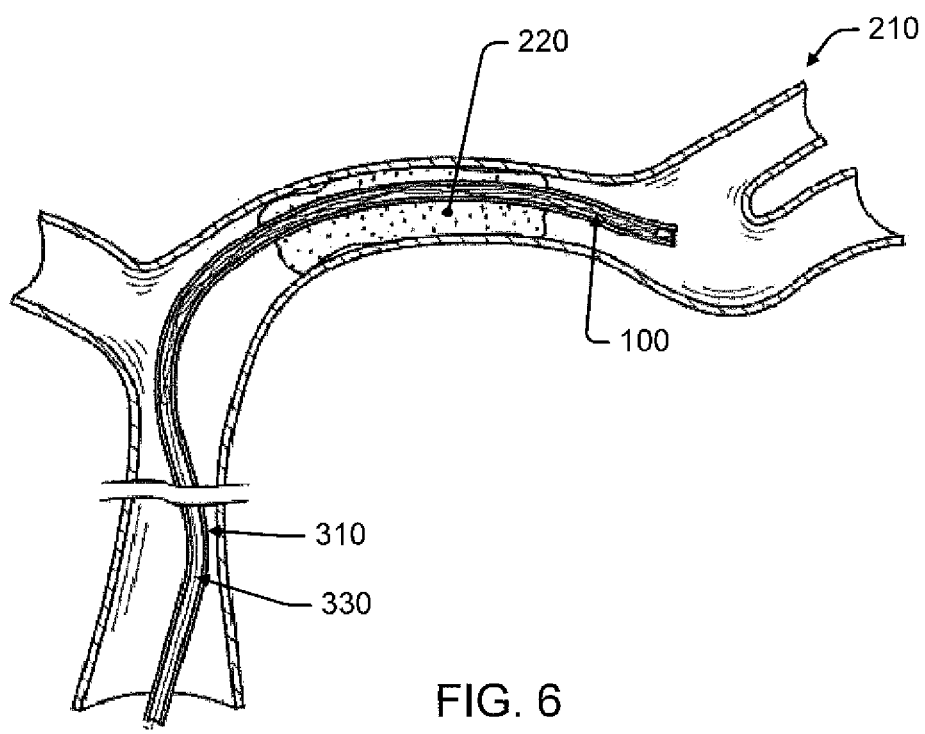
FIG. 6 depicts a cross section view of a vessel and delivery of a medical device according to some embodiments of the subject technology.

Referring to FIG. 6, the medical device 100 is advanced through the microcatheter 310 such that the distal portion 120 of the medical device 100 is disposed distal of the thrombus 220 in the anatomical lumen 210. The medical device 100 is advanced through the microcatheter 310 by a pusher or delivery wire 330 that is coupled to the proximal end of the medical device 100. The microcatheter 310 compresses the medical device 100 and thus, maintains the medical device in a compressed configuration as the medical device 100 is advanced to the treatment site.

Figure 7:
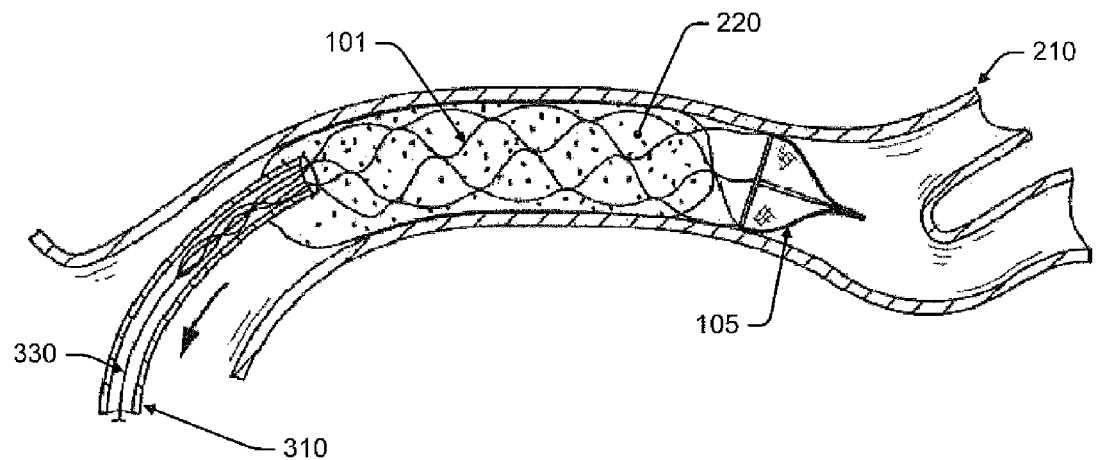
FIG. 7 depicts a cross section view of a vessel and deployment of a medical device according to some embodiments of the subject technology.
Figure 8:
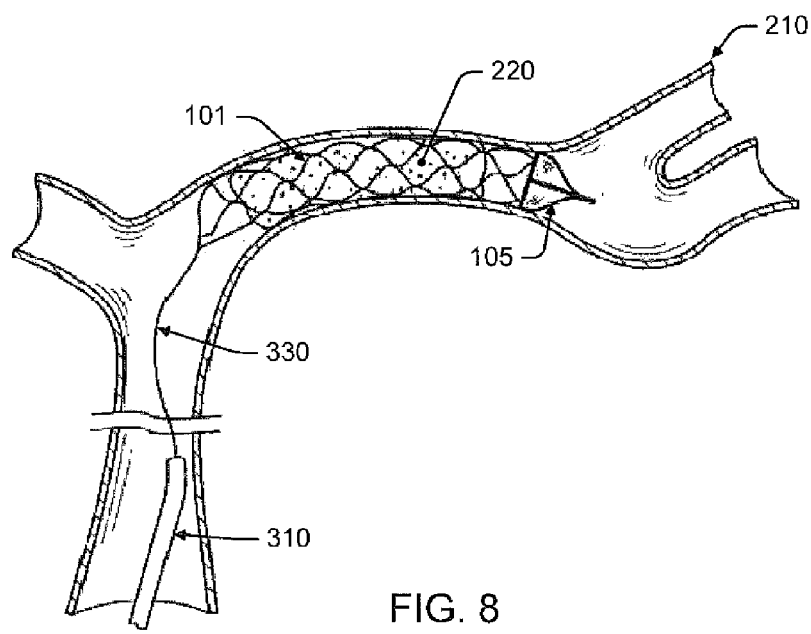
FIG. 8 depicts a cross section view of a vessel and capture of a thrombus using a medical device according to some embodiments of the subject technology.

Referring to FIGS. 7 and 8, the microcatheter 310 is withdrawn proximally relative to the medical device 100 to expose the medical device 100, thereby permitting the protector 105 and the frame 101 to expand. The frame 101 expands against a length of the thrombus 220 and engages the thrombus 220. As discussed above, the frame 101 is designed to engage and remove thrombi that are both generally soft, or malleable, or generally hard, or callous. The protector 105 expands against the inner wall of the anatomical lumen. During expansion of the frame 101, the protector 105 restricts downstream travel of any dislodged portions of the thrombus 220, referred to as secondary emboli 230, by capturing the secondary emboli in the protector 105.

Figure 9:
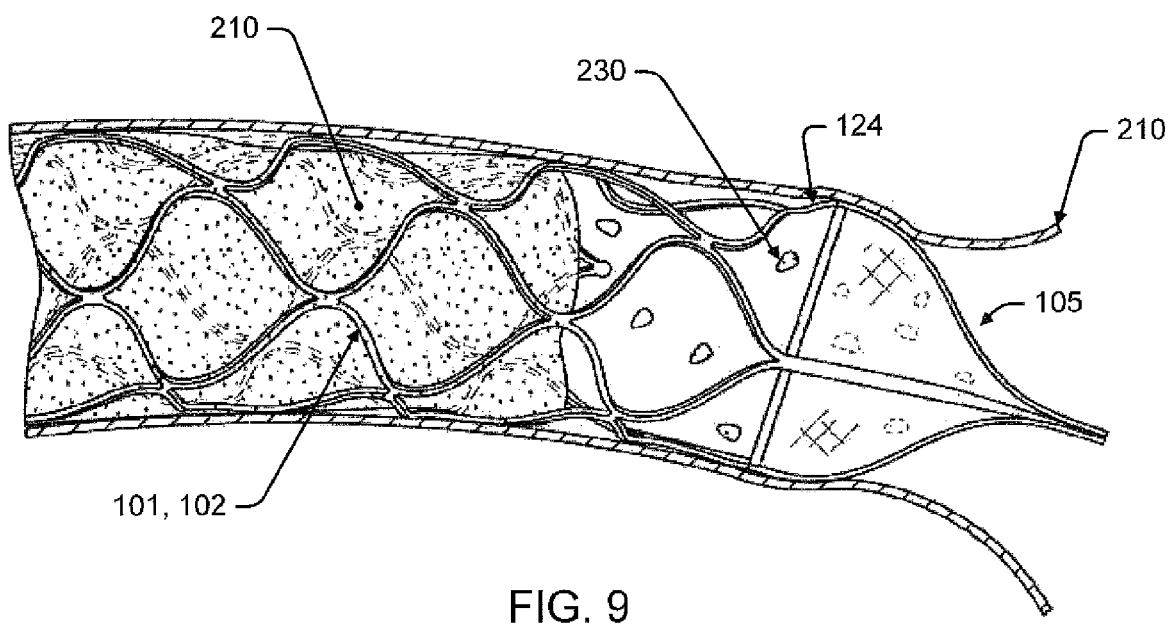
FIG. 9 depicts a cross section view of a vessel and distal portion of a medical device capturing secondary emboli according to some embodiments of the subject technology.
Figure 10:
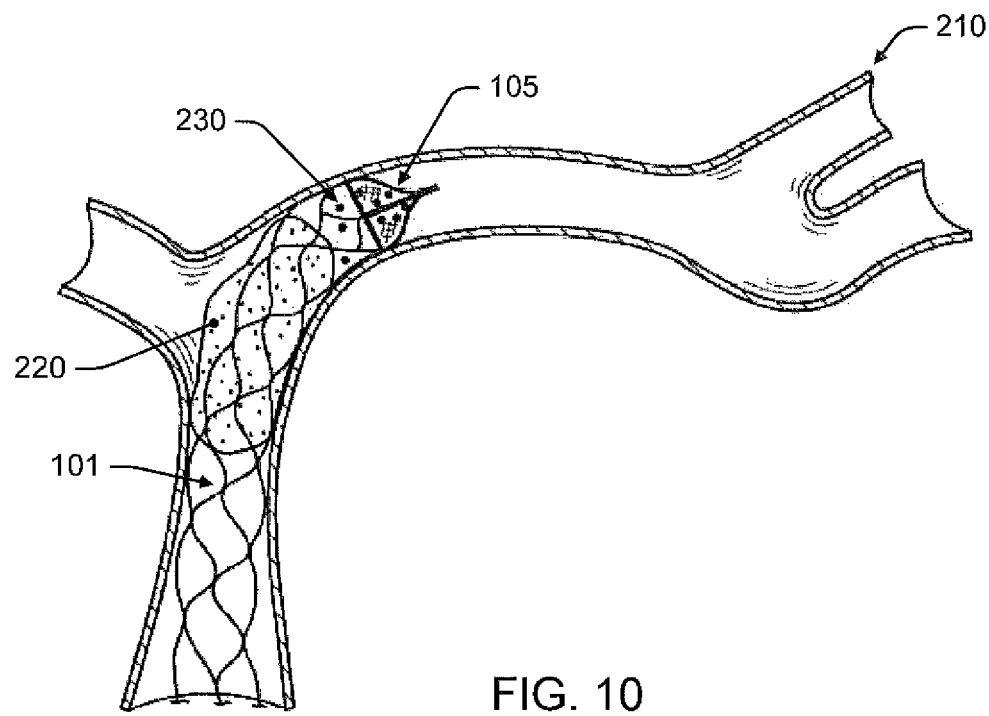
FIG. 10 depicts a cross section view of a vessel and retrieval of a thrombus using a medical device according to some embodiments of the subject technology.

Referring to FIGS. 9 and 10, the medical device 100 is withdrawn proximally, along with the thrombus 220. During retrieval of the thrombus 220, dislodgment of portions of the thrombus 220, referred to as secondary emboli 230, are captured by the protector 105, thereby preventing the secondary emboli 230 from traveling downstream and occluding other vessels or arteries. In one aspect, the probability of gaps forming between the protector 105 and the inner surface of the anatomical lumen 210 are minimized because the protector 105 is configured to independently radially expand to a diameter larger than a greatest diameter of the frame 101. Accordingly, the protector 105 captures the majority, if not all, of the secondary emboli 230.

As the medical device 100 is withdrawn proximally within the anatomical lumen 210, the sloped surface of the connecting members 124 deflect the protector 105 so that the protector 105 conforms to the inner wall of the anatomical lumen 210.

Figure 11:
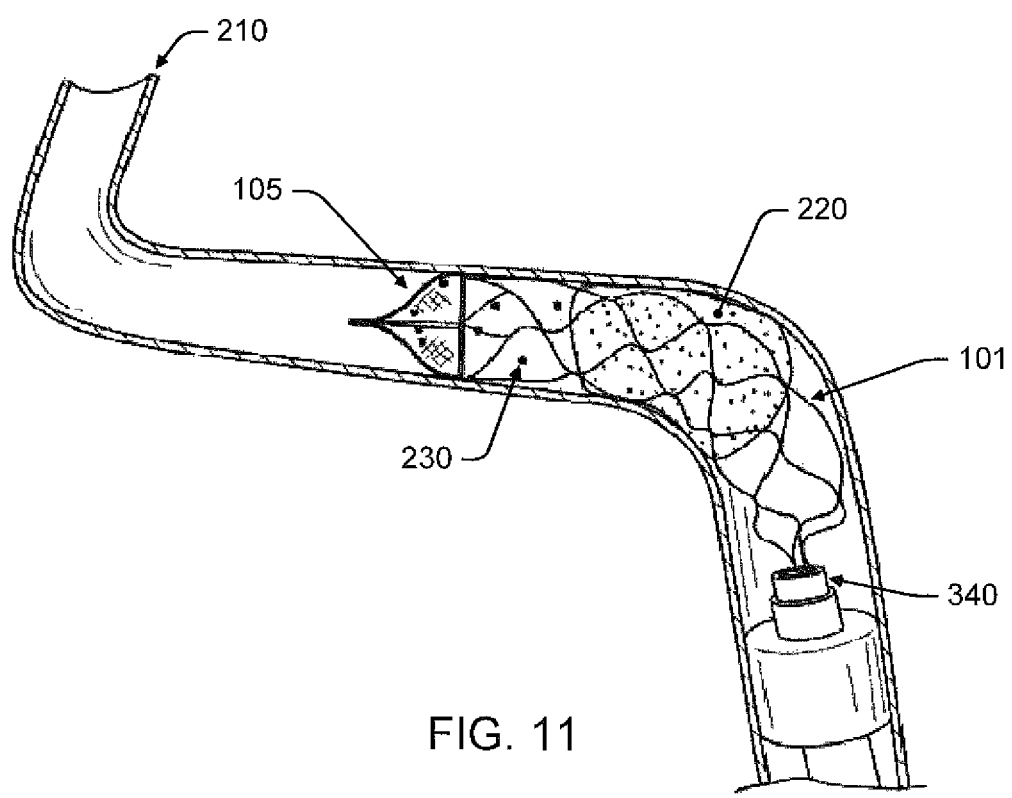
FIG. 11 depicts a cross section view of a vessel and retrieval of a thrombus using a medical device according to some embodiments of the subject technology.
Figure 12:
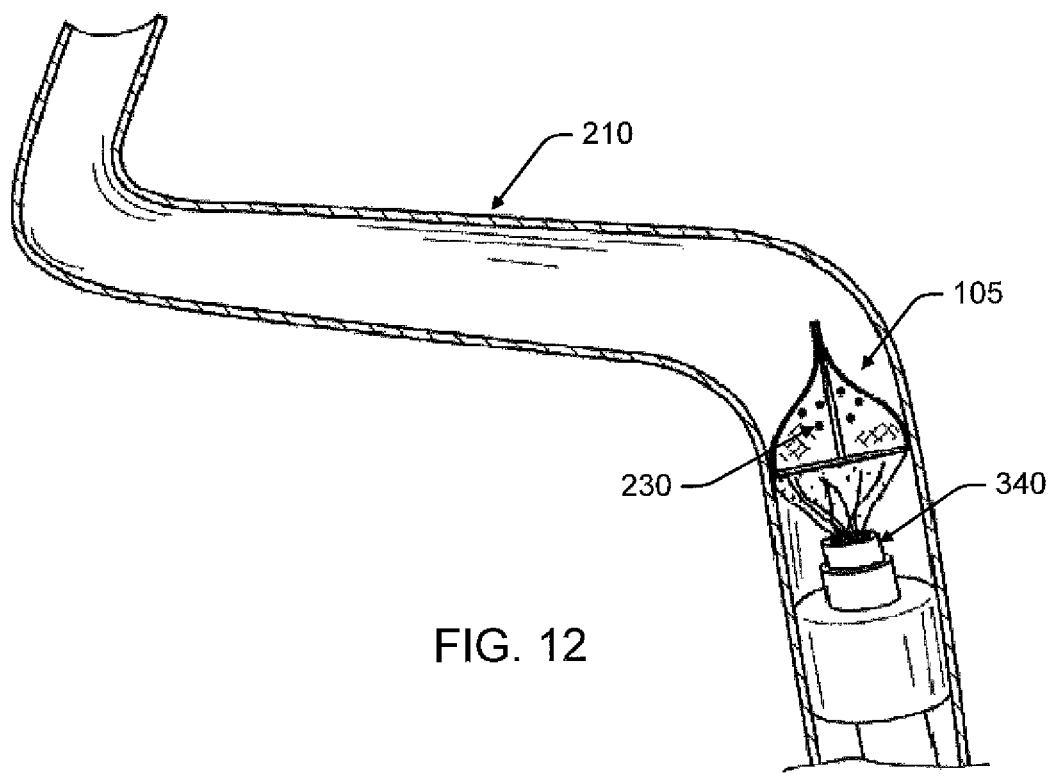
FIG. 12 depicts a cross section view of a vessel and retrieval of a thrombus using a medical device according to some embodiments of the subject technology.
Figure 13:
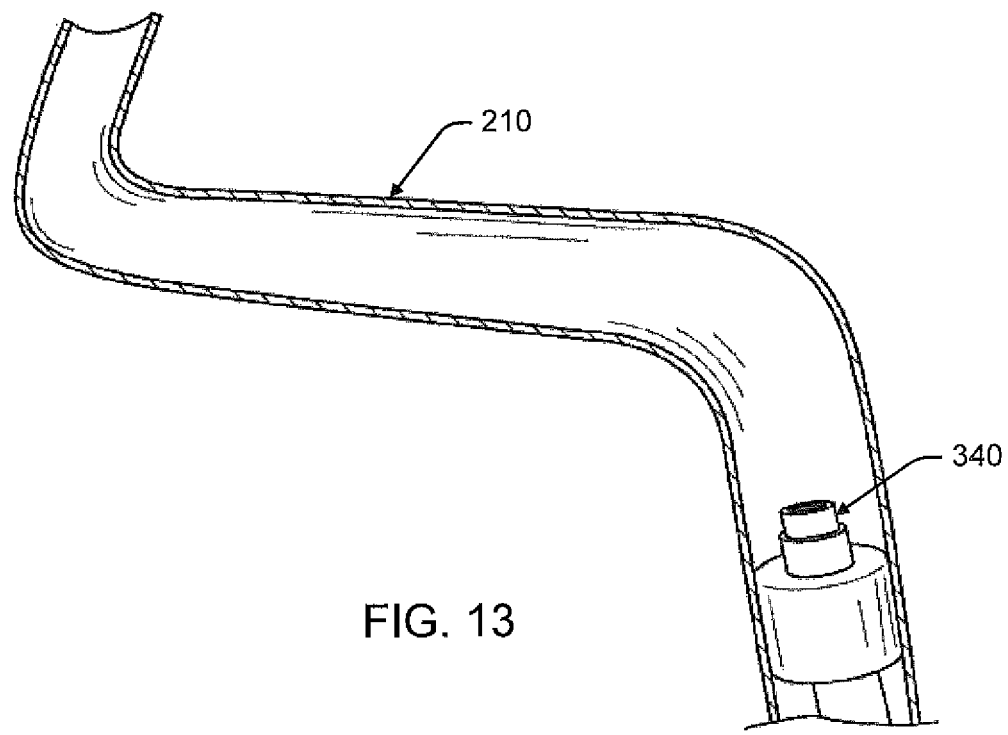
FIG. 13 depicts a cross section view of a vessel and retrieval of a thrombus using a medical device according to some embodiments of the subject technology.

Referring to FIG. 11, the medical device 100 is withdrawn proximally to the guide catheter 340. The guide catheter 340 causes the frame to collapse, with the thrombus 220 engaged therein. The thrombus 220 is thus retrieved and removed from the anatomical lumen 210. Referring to FIGS. 12 and 13, the medical device 100 is further proximally withdrawn such that the protector 105 is collapsed by the guide catheter 340, with the secondary emboli 230 captured therein. Proximally withdrawing the medical device 100 into the guide catheter 340 causes the frame 101 to collapse due to deflection of the interconnecting members 102 by the guide catheter 340. Likewise, movement of the medical device 100 into the guide catheter 340 causes the protector 105 to collapse due to deflection of the connecting members 124 by the guide catheter 340.

In one arrangement, the medical device 100 may be comprised of metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bio-analogous polymers, tungsten, tantalum, platinum, polymers, bio-polymers, ceramics, bio-ceramics, or metallic glasses. Part or all of the medical device may elute over time substances such as drugs, biologics, gene therapies, anti-thrombotics, coagulants, anti-inflammatory drugs, immuno-modulator drugs, anti-proliferatives, migration inhibitors, extracellular matrix modulators, healing promoters, re-endothelialization promoters, or other materials. In some embodiments, the medical device 100 may be formed from materials having shape memory properties. In some embodiments, the medical device 100 may be finished by processes to remove slag. In some embodiments, the medical device 100 may be subjected to a tempering treatment at temperatures customarily applied to the material so that the impressed structure is permanently established.

The medical device 100 may have various lengths and diameters. For example, the medical device 100 may have specific cross-sectional diameters, the diameters being measured when the medical device 100 is fully free to expand, ranging from about 2 mm to about 6 mm. If the medical device 100 has a diameter between 3 mm and 4 mm, it may be used in a size 18 microcatheters (i.e., microcatheters with an inner diameter of approximately 0.21 inch). If the medical device 100 has a diameter between 5 mm and 6 mm, it may be used in a size 27 microcatheters (i.e., microcatheters with an inner diameter of approximately 0.027 inch). However, other suitable cross-sectional diameters may be used without deviating from the scope of the subject technology. In some embodiments, the medical device 100 may have lengths, measured proximally to distally along the longitudinal axis of the medical device 100, ranging from 15 min to 40 mm, though other ranges and sizes are also possible.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vascular device, comprising:
   a frame attached to a distal end of a delivery wire, the frame comprising a cylindrical body formed of a plurality of interconnecting members, the interconnecting members being configured to exert a first radial force against an inner wall of an anatomical lumen when the frame has a first diameter; and
   a protector having a proximal end, a distal end, and a profile that tapers distally from a proximal cross-sectional dimension to a reduced distal cross-sectional dimension, the protector being coupled to a distal end of the frame via a plurality of connecting members, each of the connecting members extending from a distal end of a corresponding interconnecting member and converging distally to form a taper, each connecting member comprising a proximal segment and a distal segment, the proximal segment of each connecting member comprising one of (a) a cross section less than that of the distal segment of the corresponding connecting member or (b) a chain comprising a plurality of links and two individual rows coupled to each other, the proximal segments permitting the protector to radially expand independent of a radial expansion of the frame, the distal segments of the connecting members being configured to exert a second radial force, less than the first radial force, against the inner wall of the lumen when the protector has the first diameter.

2. The vascular device of claim 1, wherein a proximal portion of the plurality of connecting members form a greater cross-sectional dimension than does the cylindrical body.

3. The vascular device of claim 1, wherein a proximal end of the connecting members tapers proximally radially inward without converging to a central longitudinal axis of the frame.

4. The vascular device of claim 1, wherein each of the connecting members comprise a curve having a positive slope, negative slope, and an apex.

5. The vascular device of claim 4, wherein the positive and negative slopes are configured to facilitate deflection of the protector as the protector is advanced in the anatomical lumen.

6. The vascular device of claim 4, wherein, in an absence of external forces, the interconnecting members of the frame radially expand to a second diameter, and the connecting members radially expand to a third diameter, greater than the second diameter, wherein the third diameter is formed of apexes of each of the connecting members.

7. The vascular device of claim 1, wherein at least one proximal segment comprises (b), and the links are non-ridgidly joined to each other so that the chain is highly laterally flexible but strong in longitudinal tension.

8. The vascular device of claim 1, wherein at least one proximal segment comprises (b), and the chain is micromachined.

9. The vascular device of claim 1, wherein the protector further comprises a mesh.

10. The vascular device of claim 9, wherein the mesh comprises a plurality of pores sized such that the mesh is configured to capture emboli without preventing blood flow past the mesh.

11. The vascular device of claim 10, wherein the plurality of pores each have a pore size of about 70-200 µm.

12. The vascular device of claim 9, wherein the protector further comprises a collapsible hoop coupled to the mesh and the plurality of connecting members and disposed substantially perpendicular to a central longitudinal axis of the frame.

13. The vascular device of claim 12, wherein the hoop is coupled to the connecting members at a radial apex of the connecting members.

14. The vascular device of claim 9, wherein each of the connecting members comprise a curvature providing a sloped surface proximal of the mesh, the sloped surface being configured to assist the protector in conforming to the inner wall of the anatomical lumen as the vascular device is advanced in the lumen.

15. A vascular device, comprising:
a frame attached to a distal end of a delivery wire, the frame comprising a cylindrical body formed of a plurality of interconnecting members, the interconnecting members being configured to exert a first radial force against an inner wall of an anatomical lumen when the frame has a first diameter; and
a protector having a proximal end, a distal end, and a profile that tapers distally from a proximal cross-sectional dimension to a reduced distal cross-sectional dimension, the protector being coupled to a distal end of the frame via a plurality of connecting members, each of the connecting members extending distally from the frame, each connecting member comprising a proximal segment and a distal segment, the proximal segment of each connecting member comprising a cross section less than that of the distal segment of the corresponding connecting member, the distal segments of the connecting members being configured to exert a second radial force, less than the first radial force, against the inner wall of the lumen when the protector has the first diameter.

16. The vascular device of claim 15, wherein a proximal portion of the plurality of connecting members form a greater cross-sectional dimension than does the cylindrical body.

17. The vascular device of claim 15, wherein a proximal end of the connecting members tapers proximally radially inward without converging to a central longitudinal axis of the frame.

18. The vascular device of claim 15, wherein each of the connecting members comprise a curve having a positive slope, negative slope, and an apex.

19. The vascular device of claim 18, wherein, in an absence of external forces, the interconnecting members of the frame radially expand to a second diameter, and the connecting members radially expand to a third diameter, greater than the second diameter, wherein the third diameter is formed of apexes of each of the connecting members.

20. The vascular device of claim 15, wherein the protector further comprises a mesh.

21. The vascular device of claim 20, wherein the mesh comprises a plurality of pores sized such that the mesh is configured to capture emboli without preventing blood flow past the mesh.

22. The vascular device of claim 21, wherein the plurality of pores each have a pore size of about 70-200 nm.

23. The vascular device of claim 20, wherein the protector further comprises a collapsible hoop coupled to the mesh and the plurality of connecting members and disposed substantially perpendicular to a central longitudinal axis of the frame.

24. The vascular device of claim 23, wherein the hoop is coupled to the connecting members at a radial apex of the connecting members.

* * * * *